United States Patent [19]

Rath

[11] 4,214,341
[45] Jul. 29, 1980

[54] HYGIENIC AND COSMETIC SPONGE OR THE LIKE

[76] Inventor: Ewald Rath, Geranienstr. 5, 5600 Wuppertal 21, Fed. Rep. of Germany

[21] Appl. No.: 41,795

[22] Filed: May 23, 1979

[30] Foreign Application Priority Data

May 29, 1978 [DE] Fed. Rep. of Germany ....... 2823332

[51] Int. Cl.$^3$ .............................................. A47L 17/08
[52] U.S. Cl. .................... 15/210 R; 128/296
[58] Field of Search ................. 28/137; 128/296, 285; 15/210 R, 209 R, 209 C, 211, 212

[56] References Cited

U.S. PATENT DOCUMENTS

| | | | |
|---|---|---|---|
| 2,400,250 | 5/1946 | Mott | 28/137 |
| 2,740,405 | 4/1956 | Riordan | 128/296 |
| 2,829,648 | 4/1958 | Knapp | 128/296 |
| 3,190,289 | 6/1965 | Patience | 128/296 |

Primary Examiner—Leonard D. Christian
Attorney, Agent, or Firm—Abraham A. Saffitz

[57] ABSTRACT

In the case of a sponge for medicinal purposes, the gauze fabric cut has been folded into a small ball in the inside of which lie the edges of the cuts.

In order to achieve a machine made, homogeneously structured sponge absorbing equally well at every place without lint or projecting ends of threads, two gauze fabric cuts (2, 3) of equal length have been placed one on top of the other, whereby the inside lying cut (3) has a width of about twice and the outside lying cut (2) has a width of at least four times the diameter of the sponge. The cuts (2, 3) are folded to a pouch in the case of which the edges of the cut turned inside out, are framed by a rubber ring (5). At the same time, the inside lying cut (3) is turned inside out only with its longitudinal ends through the rubber ring (5).

4 Claims, 4 Drawing Figures

HYGIENIC AND COSMETIC SPONGE OR THE LIKE

The invention relates to a surgical sponge for medicinal, hygienic, cosmetic or similar purposes made of a fabric cut, preferably gauze fabric cut, which is folded to a pouch with an edge framed by a rubber ring and folded inside out.

Surgical sponges or tampons especially from gauze are used in the first place in the case of surgical interventions on humans or animals. Since they are used for ridding and cleaning wounds and places of surgery of blood and secretions, they must be absorbent, they must not dissolve and they must not leave threads or lint in the wound.

It has been known for a long time to use sponges from a gauze fabric which are produced by the hospital personnel or as take-home work. In this case, one starts out from cuts of square gauze fabric, which are shaped into little balls by clever foldings and interlacings, in the case of which the cut edges of the fabric discharging lint lie completely in the inside. Such a production however, is very expensive as far as costs of wages are concerned and also unsatisfactory with regards hygiene. Machine made sponges held together by a rubber ring are also know, which however are obtained at a high proportion with projecting ends of threads and which are eliminated as waste.

The solution of this task will be achieved according to the invention through the fact that the sponge is folded from double or multilayer fabric cuts and that at least two opposite terminal sections of the, or of several inside lying cut(s), is turned inside out through the rubber ring. In order to increase the homogeneousness of the sponge, it has been provided in this case preferably that the sponge consist of two superposed cuts about, or precisely of equal length, of which the cut lying on the inside has a width of about twice the diameter of the sponge and the outside lying cut is at least twice as wide as the inside lying cut, whereby the inside lying cut is turned only with its longitudinal ends inside out through the rubber ring.

Contrary to the sponges made by hand, in the case of the sponges according to the invention, the cohesion of the folded in, or of the gauze cuts turned inside out will be achieved by a rubber ring. The edges of the cuts in the case of machine production are folded inside and meet the middle area of the cuts. Since cuts of gauze fabric,—contrary to gauze bands produced with solid selvage, but being expensive—lose their loop structure very easily at the edges as a result of shifting or pulling out of their warp or filling threads, the undesirable effect results by which ends of threads when turning them inside out, will push through the enclosing fabric and will project from the sponge, whereby it is not possible to differentiate optically whether these are threads still hanging firmly or whether it is lint which is releasable and which may remain behind in a wound. In order to avoid loose ends of threads, in the case of the invention, the area of the sponge where the edges of the cuts of the gauze fabric turned inside out meet, is additionally covered up with an inserted cut. As a result of that, the number of threads is doubled per unit of area which largely takes care of the transmission (passage) for threads and lint. The inside lying part of the cut according to a preferred embodiment of the invention has a width which corresponds approximately to double the diameter of the completely shaped sponge. This measure will prevent the ends of the threads of the fabric of the inside cut to penetrate through the loops of the outside cut, since in the area of the edges of the inside cut, its ends of threads strive to fit flat against the loops of the outside cut. The width of the inside cut results from the demand for a sufficient turning inside out of the edges by the rubber ring. Since the inside cut is about as long as the outside one, its opposite, narrow sides are turned inside out by the ring which leads to a tight sponge with unshiftable layers of fabric.

In a development of the invention, provision may be made that both cuts are rectangles which mate longitudinally-concentrically and in that the two cuts have such a size that, if placed side by side, they form a square.

Starting out from a square cut of gauze fabric for a sponge made manually, one will obtain by a cut, two longitudinal rectangles of variable width which, for the machine production of the sponge, may be placed longitudinally-concentrically one on top of the other so that the bottom surface of the pouch squeezed out at first, is formed by the middle area of the cuts of the fabric.

The invention will be explained in more detail on the basis of an embodiment shown by way of example in the drawing.

Figure 1:
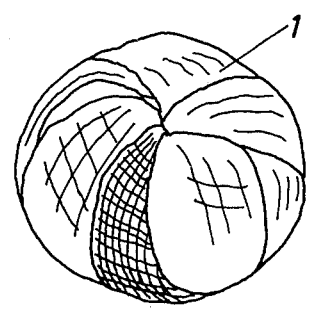
FIG. 1 shows a sponge according to the invention in perspective presentation.

FIG. 1 shows a sponge 1 folded into a small ball, which consists of two cuts 2, 3 of gauze fabric. The cuts 2, 3 are elongated rectangles of the same length c. The cut 3 lying inside of the finished sponge has a width a, which corresponds to approximately twice the diameter of the sponge 1. The outside lying cut 2 has a width b which amounts to about two and one half times the width a of the cut 3. Whenever the cuts 2, 3 are placed side by side, they will form a square with the lateral length c. The narrow cut 3 lies on top of the wide cut 2, whereby their longitudinal centers coincide.

Figure 3:
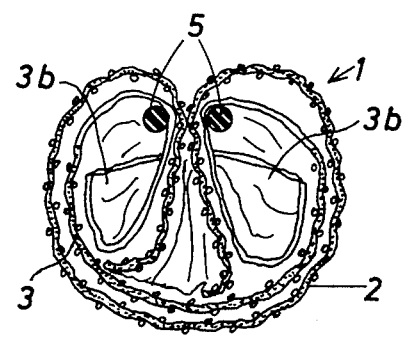
FIG. 3 shows a cut through a sponge made from the cuts acc. to FIG. 2.
Figure 2:
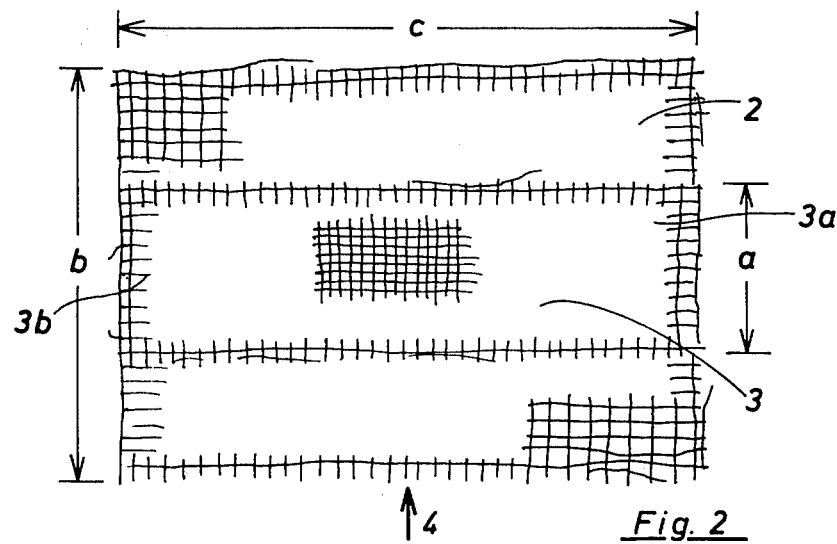
FIG. 2 shows two spread out cuts of gauze fabric according to a first embodiment at a reduced scale.

FIG. 3 shows a cut through a machine made sponge 1 from the cuts 2, 3 according to FIG. 2, whereby the cut is guided along the direction of the arrow 4 (FIG. 2), therefore perpendicularly to the longitudinal center of the cuts 2, 3. The inside lying cut 3 of the fabric fits against somewhat more than half the peripheral surface of the outside lying cut 2. The four edges of the cut 2 and the narrow edges with adjoining corner areas 3a, 3b of the cut 3, are turned inside out by a rubber ring 5 into the pouch formed by the centers of the cuts. The edges of the cuts 2, 3 meet in the area of the pouch the areas of the wall, in which areas a concentration has been provided by superimposed cuts 2, 3. Projecting ends of threads are presented thereby from pushing through the fabric and from emerging from the sponge. By selection of the dimensions of the cut, a sponge will be created which is approximately homogenous in its entire volume and has the same good absorbent qualitites independently of the place of the sponge.

Figure 4:
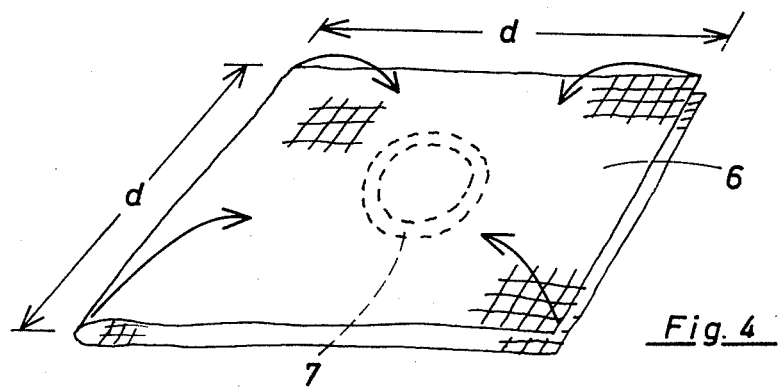
FIG. 4 shows a double folded cut of gauze fabric according to a second embodiment for the sponge.

A sponge without projecting ends of threads may also be made by machine from the cut 6 according to FIG. 4. This cut is folded in double layers for square dimension d×d. By turning the four corners inside out through a pertinent rubber ring 7, the fact that the cut has double layers, will prevent any emergence of ends of threads.

I claim:

1. A surgical sponge comprising a bulbous jacket of gauze material having a edge portion gathered together to form a constricted tubular neck at a proximal end of the jacket, said neck being turned radially inwardly of the jacket and forming a filling core of the sponge, a rubber ring disposed interiorly of the jacket and contracted onto the inturned neck thereof retaining it in the constricted inturned position, wherein the gauze material consists of two or more gauze layers forming the jacket and each of the one or the several inside lying gauze layers having at least two opposite terminal sections are gathered together with the outside lying gauze layer to form the inwardly turned neck and the filling core of the sponge.

2. Sponge as claimed in claim 1, wherein the gauze material consists of two superimposed inside and outside lying seperate gauze cuts of about the same length of which the inside lying cut has a width of about twice the diameter of the sponge and the outside lying cut is at least twice as wide as the inside lying cut, whereby the inside lying cut is turned inwardly through the rubber ring only with its longitudinal ends.

3. Sponge as claimed in claim 2, characterized in that the both inside and outside lying gauze cuts are elongated rectangles which are superimposed longitudinally and concentrically.

4. Sponge as claimed in claim 3, characterized in that the two gauze cuts are of such a size that, placed side by side, they form a square.

* * * * *